US012594359B2

(12) United States Patent
Talebpour et al.

(10) Patent No.: US 12,594,359 B2
(45) Date of Patent: Apr. 7, 2026

(54) ANTIMICROBIAL BONE CEMENT

(71) Applicants:Cyrus Talebpour, Richmond Hill (CA); Houshang Darvishi Alamdari, Kirkland (CA); Hossein Salimnia, Rochester Hills, MI (US); Rahul Vaidya, Ann Arbor, MI (US)

(72) Inventors: Cyrus Talebpour, Richmond Hill (CA); Houshang Darvishi Alamdari, Kirkland (CA); Hossein Salimnia, Rochester Hills, MI (US); Rahul Vaidya, Ann Arbor, MI (US)

( * ) Notice: Subject to any disclaimer, the term of this patent is extended or adjusted under 35 U.S.C. 154(b) by 245 days.

(21) Appl. No.: 18/335,973

(22) Filed: Jun. 15, 2023

(65) Prior Publication Data

US 2024/0157021 A1 May 16, 2024

Related U.S. Application Data

(60) Provisional application No. 63/352,998, filed on Jun. 16, 2022.

(51) Int. Cl.
*A61L 24/00* (2006.01)
*A61L 24/06* (2006.01)
(52) U.S. Cl.
CPC ........... *A61L 24/0015* (2013.01); *A61L 24/06* (2013.01); *A61L 2300/102* (2013.01); *A61L 2300/104* (2013.01); *A61L 2300/404* (2013.01); *A61L 2400/12* (2013.01)

(58) Field of Classification Search
CPC ................ A61L 24/0015; A61L 24/06; A61L 2300/102; A61L 2300/104; A61L 2300/404; A61L 2400/12; A61L 2430/02
See application file for complete search history.

(56) References Cited

U.S. PATENT DOCUMENTS

2015/0190550 A1 * 7/2015 Nusko .................... A01N 59/16
424/618

OTHER PUBLICATIONS

Talebpour et al.; ACS Sustainable Science & Engineering; 2022, 10, 4922-4928. Published Apr. 3, 2022. (Year: 2022).*

* cited by examiner

*Primary Examiner* — Jeffrey T. Palenik

(57) ABSTRACT

The subject matter of the present invention is incorporating nanostructured antimicrobial silver perovskite particles into bone cement made of Poly Methyl Methacrylate (PMMA). This is accomplished by mixing the nanostructured antimicrobial particles with the cement powder prior to the addition of liquid monomer. The spontaneous and dispersion of the antimicrobial particles in the cement during preparation allows using a small weight for weight ratio of antimicrobial particles relative to the total mass of the cement, thereby substantially preserving the antimicrobial cement's biocompatibility compared to the biocompatibility of the native cement.

20 Claims, 10 Drawing Sheets

Zone of
inhibition

Antimicrobial
particle

| Pathogen | MIC (µg/ml) |
|---|---|
| *Staphylococcus epidermitis* | 32 |
| *Staphylococcus aureus* | 4 to 8 |
| *Staphylococcus lugdunensis* | 16 |
| *Entercoccus faecalis* | 64 |
| *Pseudomonas aeruginosa* (ATCC 27853) | 2 to 8 |
| *Pseudomonas aeruginosa* | 4 |
| *Escherichia coli* | 4 to 8 |
| *Streptococcus agalactiae* | 32 |
| *Streptococcus mitis/oralis* | 8 to 16 |
| *Corynebacterium striatum* | 8 |
| *Staphylococcua caprae* | 8 |
| *Staphylococcus captitis* | 4 |
| *Cutibacterium acnes* | 16 |
| *Candida parapsilosis* (ATCC 22019) | 1 to 2 |
| *Candida parapsilosis* (ATCC 90028) | 8 |
| *Candida parapsilosis* | 4 |
| *Candida albicans* | 4 |
| *Serratia marcescens* | 32 |
| *Enterobacter cloaceae complex* | 32 |

FIGURE 3A.

| Samples | Ag concentration (ppm) |
|---|---|
| Control - 5 days | 0.001 |
| 4 wt %AgNbO$_3$ - 5 days | 0.037 |
| Control - 12 days | 0.002 |
| 4 wt %AgNbO$_3$ - 12 days | 0.125 |
| Positive control: 2 ppm Ag | 2.021 |
| Control - 28 days | 0.002 |
| 4 wt %AgNbO$_3$ - 28 days | 0.174 |
| Control - 45 days | 0.001 |
| 4 wt %AgNbO$_3$ - 45 days | 0.223 |

FIGURE 5.

| | PMMA | PMMA containing 2% NS_AgNbO$_3$ | PMMA containing 4% NS_AgNbO$_3$ |
|---|---|---|---|
| Compressive yield strength (%) | 81.26 ± 3.33 | 81.04 ± 0.66 | 74.57 ± 0.87 |
| Strain at compressive yield strength (%) | 8.30 ± 0.44 | 7.92 ± 0.19 | 7.83 ± 0.34 |
| Compressive strength (MPa) | 162.85 ± 23.67 | 149.21 ± 22.13 | 122.87 ± 11.36 |
| Strain at compressive strength (%) | 56.96 ± 2.36 | 54.43 ± 3.16 | 53.42 ± 3.66 |

FIGURE 7.

| Strain (%) | Cycles (N) - PMMA | Cycles (N) - PMMA loaded with 2 % NS_AgNbO$_3$ | Cycles (N) - PMMA loaded with 4 % NS_AgNbO$_3$ |
|---|---|---|---|
| 0.42 | 8618 | 4314 | 3984 |
| 0.37 | 14624 | 19851 | 9338 |
| 0.31 | 245443 | 291243 | 103785 |
| 0.26 | 386697 | 540819 | 697370 |
| 0.21 | 660586 | > 1641647 (Not broken) | 1605894 |

FIGURE 8.

|  | Rockwell L hardness - pure PMMA | Rockwell L hardness – PMMA loaded with 2 % NS_AgNbO$_3$ | Rockwell L hardness - PMMA loaded with 4 % NS_AgNbO$_3$ |
|---|---|---|---|
| Specimen No. 1 | 94.92 ± 3.40 | 90.86 ± 2.62 | 89.40 ± 3.08 |
| Specimen No. 2 | 88.84 ± 1.49 | 95.26 ± 2.83 | 88.04 ± 1.96 |
| Specimen No. 3 | 91.64 ± 3.43 | 92.00 ± 1.98 | 89.38 ± 2.90 |
| Average | 91.8 | 92.7 | 88.9 |

FIGURE 9.

ANTIMICROBIAL BONE CEMENT

SUMMARY OF THE INVENTION

The invention relates to an antimicrobial bone cement characterized by containing nanostructured particles comprising an antimicrobial silver perovskite, where the weight of the nanostructured antimicrobial silver perovskite particles is in the range of 1% to 10% of the total weight of the cement. According to various embodiments of the invention, the nanostructured antimicrobial silver perovskite is either $AgNbO_3$ or $AgTaO_3$ with specific surface area of at least 1 $m^2/g$ and the silver release rate of less than 0.1% of their total weight over 24 hours into deionized water at room temperature.

According to one embodiment the preparation method of the cement consists of the steps of mixing nanostructured antimicrobial silver perovskite particles with the dry component of the cement thus obtaining a first mixture and adding the liquid component to the first mixture.

In a selected embodiment the bone cement is polymethyl methacrylate (PMMA) and the dry component consists of an acrylic polymer and an initiator capable of initiating a polymerization reaction and the liquid component consists of an acrylic monomer and a polymerization inhibitor.

FIELD OF THE INVENTION

This disclosure relates to providing permanent antimicrobial activity to bone cements without substantially compromising their biocompatibility.

BACKGROUND OF THE INVENTION

Using bone cements to fix joint arthroplasties or as a temporary spacer for two-stage revision of joint arthroplasties is widely practiced in orthopedics. The most common bone cement, polymethyl methacrylate (PMMA), is an acrylic resin polymer and is obtained by mixing methyl methacrylate (MMA) monomer with pre-polymerized polymethyl methacrylate particles in the presence of an initiator, an activator, and a stabilizer. As the application of cement is prone to bacterial infections, it is often loaded with conventional antibiotics. This practice is associated with risks such as emerging antimicrobial resistance and the gradual loss of efficacy due to ever decreasing antimicrobial activity through the depletion of the antibiotics from the cement. Replacing conventional antibiotics with relatively safe and broad-spectrum antimicrobial silver compounds, such as silver nanoparticles or silver salts has been suggested to counter some of these shortcomings and limitations. However, this approach may perturb the cement's biocompatibility by the release of silver ions. In addition, the long-lasting antimicrobial action of the common silver compounds for countering delayed infections has not been demonstrated.

Thus, there is a need for supplying bone cements with broad-spectrum and long-lasting antimicrobial activity without substantially impacting their biocompatibility.

BRIEF DESCRIPTION OF THE DRAWINGS

Embodiments will now be described, by way of example only, with reference to the drawings, in which:

FIG. 3A illustrates the MIC value of the typical nanostructured $AgNbO_3$ powder described in the specification against common pathogens encountered in arthroplasty infections.

FIG. 5 presents the silver release rate from bone cement discs containing 4% w/w nanostructured antimicrobial perovskite ($AgNbO_3$) particles.

FIG. 7 Presents the average compressive yield and strength of 5 replicate samples of PMMA, PMMA containing 2% w/w nanostructured antimicrobial perovskite ($AgNbO_3$) particles, and PMMA containing 4% w/w nanostructured antimicrobial perovskite ($AgNbO_3$) particles.

FIG. 8 Presents the number of cycles before material failure under different strain conditions of fatigue testing, for PMMA, PMMA containing 2% w/w nanostructured antimicrobial perovskite (NS_$AgNbO_3$) particles, and PMMA containing 4% w/w nanostructured antimicrobial perovskite (NS_$AgNbO_3$) particles.

FIG. 9 Presents the Rockwell L hardness, for PMMA, PMMA containing 2% w/w nanostructured antimicrobial perovskite (NS_$AgNbO_3$) particles, and PMMA containing 4% w/w nanostructured antimicrobial perovskite (NS_$AgNbO_3$) particles.

DETAILED DESCRIPTION

Figure 1:
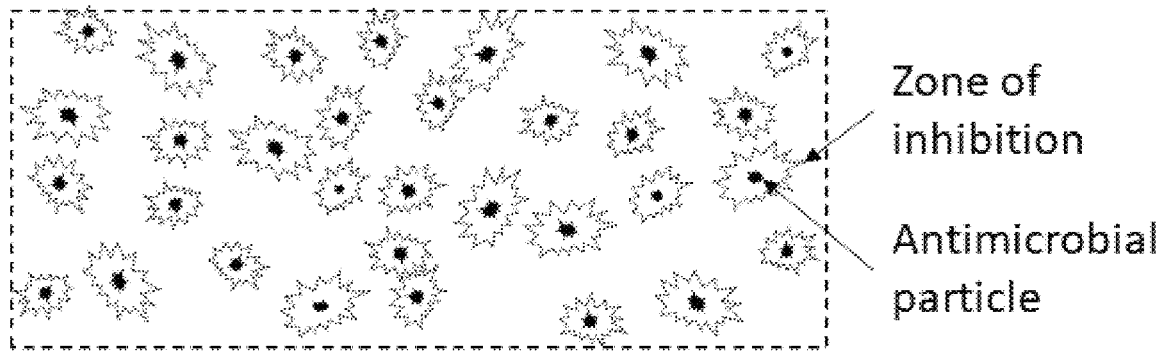
FIG. 1 schematically presents the surface at bone-cement interfaces which has been prepared according to the methods of the present invention. Each of the exposed antimicrobial particles is associated with a 'zone of inhibition'. A microbial cell located in the zone of inhibition is likely to move to the proximity of the antimicrobial particle and lose its ability to proliferate.

Various embodiments and aspects of the disclosure will be described with reference to details discussed below. The following description and the associated drawings are illustrative of the disclosure and are not to be construed as limiting the disclosure. Many specific details are described to provide a thorough understanding of various embodiments of the present disclosure. However, in certain instances, well-known or conventional details are not described in order to provide a concise discussion of the embodiments of the present disclosure.

As used herein, the term "biocompatibility" refers to the property of a material in terms of its ability to function without producing significant toxic or immunological response when exposed to human tissue or bodily fluids.

As used herein, the term "conventional silver" refers to silver compounds in the form of soluble silver salts such as $AgNO_3$ and silver (or silver oxide) nanoparticles.

As used herein, the term "antimicrobial" refers to a compound which kills or inhibits the proliferation of at least a class of microbial cells.

As used herein, the term "Minimum inhibitory concentrations (MICs)" is defined as the lowest concentration of an antimicrobial that will inhibit the visible growth of a microorganism after overnight incubation.

As used herein, the term "corrosion resistant" describes the ability of a powdered silver containing compound to resist releasing silver ions to the environment by chemical or electro-chemical reactions. We quantify this property by RSRR (Relative Silver Release Rate), which is the ratio of the level of silver ions released from the compound to a volume of deionized water to the silver ions released from $Ag_2O$ nanoparticles having a specific surface area of about 1 $g/m^2$, with similar amount of silver content and poured into similar volume of deionized water, over similar period of time. For example, if 248.8 mg of the $AgNbO_3$ powder is poured into 1 L of deionized water and 115.9 mg of the $Ag_2O$ powder is poured in another 1 L of deionized water and after 2 days of storing in room temperature the concentration of the released silver ions is found from these compounds to be respectively 0.1 mg/L and 10 mg/L, then RSRR for the $AgNbO_3$ powder is 0.01 or 1%. Thus, corrosion resistance, as used in the present disclosure, is a relative term. The acceptable upper limit of RSRR depends on application. In embodiments of the present disclosure, we require RSRR<20%.

As used here, the "specific surface area" is a property associated with powders. Thus, when speaking of "a solid that includes nanostructured particles with a specific surface area in a specified range", we mean that the powder used to incorporate the particles in the solid during preparation had the said specific surface area. One may also think of a way, such as dissolution of the matrix, to separate sufficient numbers of the particles from the solid, thus obtaining a powder to measure the "specific surface area" employing a measurement technique, such as the one presented in the current disclosure.

As used here, a bone cement generally refers to a material that is used to fill voids or gaps in bones or anchor artificial joints, such as hip joints, knee joints, shoulder, and elbow joints. However, in the context of present invention bone cement indicates a bone cement based on polymethyl methacrylate (PMMA).

As used here, the liquid component of the bone cement typically consists of the liquid monomer of methyl methacrylate (MMA), an accelerator, such as an amine (e.g., N,N-dimethyl-p-toluidine), and a stabilizer, such as hydroquinone (HQ) that is added to prevent premature polymerization of the liquid monomer.

As used here, the dry component of the bone cement typically includes an acrylic polymer, such as polymethyl methacrylate (PMMA) in the form of small polymer beads, a polymerization initiator, such as benzoyl peroxide, to trigger polymerization when mixing occurs, and a radiopaque agent such as zirconia ($ZrO_2$) or barium sulfate ($BaSO_4$).

As used herein, the "Nanostructured aggregate" is a collection of crystallites whose dimension falls between 1-1000 nanometers. Thus, by the term nanostructured $AgNbO_3$ we mean aggregates of sub-micron $AgNbO_3$ crystallites.

As used herein, the amount of a "Nanostructured antimicrobial aggregate" particle in an antimicrobial cement is specified with the weight-to-weight ratio (w/w) of the particles relative to the cement's dry component. Thus, 4% w/w cement, or cement loaded with 4% of particles, means a particle containing cement whose dry component was mixed with 4% w/w of particles before adding the liquid component.

As used herein, the "High energy ball milling" is a process in which a powder mixture confined within an oscillating crucible is subjected to impact force from collision with metallic or ceramic balls. The process is used to fracture fragile crystals in the powder or deform the ductile particles plastically.

As used herein, the "Low energy ball milling" or "Attrition milling" is a process in which a powder mixture confined within a stationary crucible is subjected to shear force from the attrition action of metallic or ceramic beads. In this process the specific surface of the powder is increased.

Bone cements are widely used in orthopedic surgery for the sealing of prostheses, treatment of vertebral compression fractures, as filling material for vertebroplasty, and as a grouting agent for permanent fixation of implants to bone. Bone cement is directly prepared in the operating room during surgery by mixing two components: (1) A liquid component that typically consists of the liquid monomer of methyl methacrylate (MMA), an accelerator, such as an amine (e.g., N,N-dimethyl-p-toluidine), and a stabilizer, such as hydroquinone (HQ) that is added to prevent premature polymerization of the liquid monomer. (2) A powder component that usually includes an acrylic polymer, such as polymethyl methacrylate (PMMA) in the form of small polymer beads, a polymerization initiator, such as benzoyl peroxide, to trigger polymerization when mixing occurs, and a radiopaque agent such as zirconia ($ZrO_2$) or barium sulfate ($BaSO_4$).

When the liquid component is mixed with the powder or dry component, the liquid monomer wets the polymeric powder and the partial dissolution and swelling of the solid polymer beads in the liquid monomer starts. The polymerization reaction is initiated as soon as the two components are mixed and shortly afterwards the hardening phase starts.

Fixation with bone cement creates tissue-cement interfaces, where post-surgical bacterial infections may occur by bacterial proliferation and biofilm formation at the cement-tissue interface. Currently, the main strategy for preventing infections is mixing conventional antibiotics with the cement. The added antibiotic must have some key qualities: (a) broad-spectrum antibacterial activity (effective against Gram-positive and Gram-negative bacteria); (b) lack of resistance in pathogenic bacteria; (c) water solubility; (d) non-toxic or allergenic; (e) thermostability against the temperature rise during the exothermic polymerization reaction of the cement. The most frequently used antibiotics are gentamicin, tobramycin, erythromycin, and vancomycin. To achieve a broader spectrum of action and efficacy it is usual to combine two or more antibiotics, exploiting their different mechanisms and possible synergistic effects. Typically, the amount of added antibiotics is not more than 3 g (for 40 g of dry component), and the use of cements loaded with more than 5% of antibiotic is only recommended for spacers.

The advantage of antibiotic loaded PMMA for reducing the infection has been documented in published literature. Based on the available clinical evidence, a meta-analysis has concluded that antibiotic-loaded bone cement may reduce the infection risk by 50% [Parvizi et al. 'Efficacy of antibiotic-impregnated cement in total hip replacement', *Acta Orthop* 2008; 79: 335-341.]. However, the merits of antibiotic-loaded bone cements are still debated, particularly in regard to the antibiotic resistance and its lack of long-term efficacy [Bistolfi, Alessandro, et al. "PMMA-based bone cements and the problem of joint arthroplasty infections: status and new perspectives." *Materials* 12.23 (2019): 4002.]. PMMA bone cement loaded with more stable antibacterial agents, is a potential replacement to antibiotic loaded PMMA and may mitigate the drawbacks associated with suboptimal concentrations of antibiotics and the risks of antimicrobial resistance and infection many days after performing surgery. Silver compounds are among candidate agents.

The antimicrobial activity of silver appears to be mediated through the release of silver ions. These ions are thought to prevent bacterial cell proliferation via processes such as alterations of cell membrane permeability, inhibition of enzymatic activities and DNA synthesis, and interruption of intracellular signal transduction. There are publications regarding the use of conventional silver compounds as an antimicrobial agent. Studies have shown a good antimicrobial effect of bone cements loaded with compounds that release silver ions and no significant short-term cytotoxic effect. However, there are concerns about the potential long-term health risks of such compounds: 1) Long-term effects of exposure to silver ions released from typical silver ion releasing PMMA have not been fully evaluated. 2) Over the long term, compounds that release silver ions may stimulate the development of antimicrobial resistance: typical silver ion-releasing compounds are expected to lose antimicrobial activity over time. Thus, the bacterial cells arriving at the interface long after the surgery will face lower doses of ever depleting silver, and mutants resistant to the antimicrobial activity of silver can emerge. 3) One study has indicated that incorporation of ion-releasing silver nanoparticles significantly decreased the tensile strength of the polymer, perhaps due to incomplete wetting of the nanoparticles by resin [Hamedi-rad, F. Effect of Silver Nanoparticles on Tensile Strength of Acrylic Resins. *Dental research, dental clinics, dental prospects* 2015, 9, No. 1, 40-43.].

To alleviate the above-mentioned issue, we incorporated nanostructured $AgNbO_3$ antimicrobial particles (hitherto known as NS—Ag), into the cement precursor powder components. The procedure involves grinding pre-polymerized PMMA beads and benzoyl peroxide (BPO) initiator with NS—Ag. Mixing the powder with the liquid component results in a homogeneous distribution of the NS—Ag particles within the cement without being fully shielded on the interface by a polymer layer, which might lead to diminishing antimicrobial activity at the surface. As the cement's surface is only partially covered by the antimicrobial particles, the surface is expected to preserve the biocompatibility and the healing features of the original cement surface. The experimental results which will be presented below confirms our innovative approach.

One of the major intellectual merits of the current invention is related to the synthesis technique of NS—$AgNbO_3$, which is synthesized through a series of thermo-mechano-chemical treatments. The resulting material in powder form is a nanostructured ceramic with a perovskite structure ($ABO_3$), having a mean crystallite size in the order of 10 nm. The agglomerate size can be tailored in the last step of the synthesis The process also allows engineering of the microstructure to provide hard agglomerates with a high density of grain boundaries. We speculate that the presence of the grain boundaries within the particles allows the particles to slightly vary the oxygen content. Variation of oxygen content imbalances the charge neutrality, which is in turn balanced by different oxidation valances of Ag (or Nb). The high density of grain boundaries significantly increases the oxygen mobility within the material and facilitates a continuous change in oxidation valance of the silver. Thus, if these particles are homogeneously dispersed inside of and on the surface of the cement when it hardens, each particle will create an inhibition zone for bacterial growth inhibition. A microbial cell located in this zone loses its ability to proliferate and to form biofilm. The concept may be understood better by referring to the schematics of FIG. 1.

In FIG. 1 the substrate is a representation of bone cement in which the antimicrobial particles are tightly incorporated and dispersed such that the cement's surface is only partially covered with them. Associated with each of these particles, we have schematically shown a 'zone of inhibition'. Each zone can be thought of as a sufficiently small area such that when a microbial cell is located in it, it is likely to move to the proximity of the antimicrobial particle through different types of motility mechanisms where it will lose its viability. This requires that the antimicrobial particles are preferred to exert their antimicrobial activity through contact. Here by the word contact we mean a sufficiently small distance within the geometrical confines of the zone of inhibition.

The concept represented by FIG. 1, also implies that a microbial cell located outside of inhibition zones can proliferate and form microcolonies (colonies with sizes often too small to be visible). The extracellular matrix (ECM) produced by bacteria in the microcolony constitutes a barrier with the antimicrobial particles and mitigates their antibacterial activity. In other words, if the biomass of the ECM is sufficiently high, it can effectively shield the antimicrobial particles and the microcolony can develop into biofilm. Thus, we expect a minimum surface concentration of the antimicrobial particles to inhibit the formation of biofilms as will be illustrated after describing the candidate antimicrobial particles. For a good antimicrobial surface, the surface concentration of the particles in FIG. 1 is such that the zones of inhibitions overlap, and the microbial proliferation is inhibited. A bone cement with too large a distance between the antimicrobial particles may lose its antimicrobial property since no or sub lethal silver ion will be released from the said antimicrobial nanoparticles to the environment. A bone cement with too small distance between the antimicrobial particles is not preferred due to its risk for proliferation of the human cells and for deterioration of the mechanical properties of the cement.

Returning to the subject matter of the current invention, our preferred antimicrobial particles are NS—$AgNbO_3$ or NS—$AgTaO_3$ or a mixture of both, at least one of them having perovskite structure. Our experimental observations have indicated that these particles exhibit long-lasting broad-spectrum antimicrobial activity, very long shelf life, and the ability to tolerate harsh environments: high and low pH (3 to 10), high temperatures (up to 400° C.), high chlorine concentrations, and exposure to light (IR/visible/UV). The stable crystalline structure of $AgNbO_3$ or NS—$AgTaO_3$ makes them corrosion resistant, meaning that they release negligible amounts of silver ion into the aqueous environment. Despite this, their antimicrobial activity (minimal inhibitory concentration; MIC), is similar to that of silver oxide or silver nanoparticles that have at least a 50-60 times greater ion release rate [Talebpour, C., et al. "Nondegradable Antimicrobial Silver-Based Perovskite." *ACS Sustainable Chemistry & Engineering* 10.15 (2022): 4922-4928.]. The measured MIC values, for properly particles (as will be described below) in suspended form is in the range of 4-16 µg/mL for the following organisms: methicillin-resistant *Staphylococcus aureus* (MRSA), multidrug-resistant (MDR) *Pseudomonas aeruginosa*, MDR *Klebsiella pneumoniae*, MDR *Acinetobacter baumannii, Clostridium difficile, Legionella pneumophila*, and *Candida albicans*. We speculate that the antimicrobial action of these particles depends on something other than silver ion release. One possible mechanism of action may be related to the ease of oxygen exchange along the grain boundaries and the continuous change of silver oxidation valence in contact (close proximity) with microorganisms. This facilitates the continuous interactions with microorganisms and enhances the generation of Reactive Oxygen Species (ROS), lethal for microorganisms. It is understood that something other than ROS may be responsible for antimicrobial activity, but this is not a limitation to the current invention.

The concept of zone of inhibition is merely a means for understanding the approach and determination of its size is not a requirement for actual implementation. In one implementation, we add different amounts of the nanostructured antimicrobial particles to the cement and perform in vitro tests and empirically determine two requirements: 1) Efficacy in terms of killing prevalent microbial species in bone cement related applications according to the method of Example 7 and 2) ensuring biosafety as determined by the method of Example 8. Accordingly, a range of acceptable amounts in terms of the weight ratio (w/w) of the antimicrobial particles to the weight of the cement's dry component is determined.

Perovskite compounds are typically synthesized by two methods: the solid-state method (also known as ceramic method) and wet chemical reaction method, i.e., sol-gel method. In the ceramic method the perovskite compound is synthesized from metal-oxide precursors by high-temperature heat treatment.

The sol-gel method is commonly used for the synthesis of perovskite compounds and is a simple method for obtaining perovskites with relatively high surface areas. In this method, the solution "sol", which includes the salts of metals A and B, gel precursor, and appropriate additives, are gradually converted to a gel with methods such as heating or freeze drying. Then, the dried gel is calcined, and homogeneous perovskite compound is obtained. The intimate and homogeneous mixture of the precursors in the gel results in low diffusion distance, which allows synthesizing the perovskite at relatively low temperatures, thus inhibiting undesired grain growth.

One example implementation of synthesizing nanostructured $AgNbO_3$ by sol-gel method is presented in Example 1A. In this case the calcination was performed at a temperature of 550° C. for 2 h. This temperature must be carefully chosen to complete the reaction of the precursors while keeping the final crystallite size as small as possible. Too low a temperature results in the presence of unreacted precursors and too high a temperature results in excessive crystallite growth. According to our experiments, the preferred range of the calcination temperature is selected in the range of 500° C. to 700° C. and the calcination time is in the range of 1 h to 3 h.

In preferred embodiment, we synthesize nanostructured $AgNbO_3$ employing the ceramic method followed by mechanical treatment. This method is easily scalable, requires low-cost raw material (oxides) and leaves no waste. An example implementation, which is given in Example 1B, consists of the following steps: 1) mixing the $Ag_2O$ powder with stoichiometric amounts of either $Nb_2O_5$ or $Ta_2O_5$, 2) heating the mixture to a formation temperature in the range of 800° C. and 1100° C., 3) staying at the formation temperature for about 4 hours, 4) gradually cooling down the product to room temperature to obtain a polycrystalline solid, 5) subjecting the polycrystalline solid to high energy ball milling at least 5 minutes to obtain a nanostructured silver perovskite oxide, and 6) optionally subjecting the product to low energy ball milling for a duration of at least 10 minutes. The synthesis parameters (formation temperature and the durations of high and low energy ball milling) may be optimized to obtain nanostructured particles with higher antimicrobial activity. A set of such optimum parameters are employed in the method of Example 1B.

Employing either method of synthesis, as described above, we obtained nanostructured particles and characterized them in terms of three parameters: average size, specific surface area, and silver ion release rate. Examples 2A, 2B and 2C are among exemplary approaches for measuring these parameters.

The range of these parameters for either NS—$AgNbO_3$ or NS—$AgTaO_3$ nanostructured particles intended to be incorporated into the bone cement according to the implementations of the current disclosure are the following.

The average particle size may be selected in the 10 nm to 4000 nm range, or 50 to 2000 nm range or 100 nm to 2000 nm or 100 to 1000 nm range.

The specific surface area may be selected in the 1 $m^2/g$ to 40 $m^2/g$ range, or 2 $m^2/g$ to 20 $m^2/g$ range or 4 $m^2/g$ to 10 $m^2/g$ range.

The range for the Relative Silver Release Rate (RSRR) is between 0.1% to 50%, between 1% to 20%, and between 1% to 15%.

After synthesizing the nanostructured antimicrobial particles (either NS—$AgNbO_3$ or NS—$AgTaO_3$) they can be used for making antimicrobial bone cement. For this end, the particles are well mixed with the dry component of bone cement, at the application site. Alternatively, due to the stability of the dry component in combination with nanostructured antimicrobial perovskite particles, the mixture may be prepared and packaged in a manufacturing site employing appropriate quality control. This is associated with considerable saving time for the surgical team as well as reduction in operation room time.

When this powdered mixture is mixed with the separately kept liquid monomer component, the partial dissolution and swelling of the solid polymer beads in the liquid monomer starts and shortly afterwards the hardening phase starts. Consequently, the nanostructured antimicrobial perovskite particles are dispersed inside of and on the surface of the cement when it hardens. Each particle in essence creates an inhibition zone for bacterial growth inhibition. A microbial cell located in this zone loses its ability to proliferate and to form biofilm. One particular aspect of the current invention is that the nanostructured antimicrobial perovskite particles ended up at the cement's interface are not fully covered by PMMA polymer and exhibit sufficient antimicrobial activity at a relatively small w/w ratio of the particles to the cement's mass. In addition, the distribution of nanostructured antimicrobial particles on the interface is sufficiently uniform. Without being limited to the theory, we speculate that this homogenization during cement formation spontaneously results from hydrophilic interaction. The result is that the w/w ratio of the antimicrobial particles to the cement's mass can be kept between 0.5 to 10%, or 1 to 8% or 1 to 4%. The appropriate ranges may be selected by performing antimicrobial activity tests, e.g., according to the method of Example 7, and mechanical tests, e.g., according to the methods of Examples 8 to 10.

Now, we describe an exemplary implementation of the invention. It is understood that the used parameters are selected for illustration purpose and should not be taken as limitation.

Figure 2:
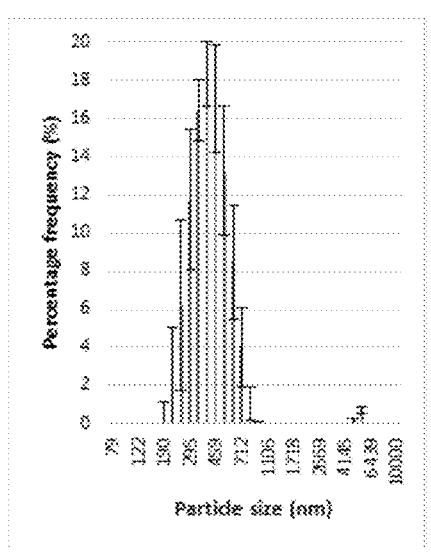
FIG. 2 illustrates the size distribution of a typical batch of nanostructured antimicrobial perovskite particles ($AgNbO_3$) used for exemplary embodiments of the current invention.

Nanostructured $AgNbO_3$ particles were prepared according to the method of Example 1B. The particles were characterized according to the methods of Examples 2A, 2B and 2C. Their particle size distribution, as presented in FIG. 2. The average particle size was 438 nm. The particles had a specific area of 5.3 $m^2/g$ and the Relative Silver Release Rate in powder form was 8% after 1 day and 5% after 35 days.

Figure 3B:
FIG. 3B presents the photos of overnight incubated plates on which the antimicrobial activity of nanostructured $AgNbO_3$ particles against Staphylococcus aureus ATCC 29213 was assessed employing agar dilution method.

The nanostructured $AgNbO_3$ particles were also characterized in terms of their antimicrobial activity according to the method of Example 3A for different pathogenic organisms typically involved in arthroplasty infections and the result was presented in FIG. 3A.

We also measured the antimicrobial activity of the nanostructured $AgNbO_3$ particles by agar dilution according to the method of Example 3B. The photo of plates after overnight incubation in the case of *Staphylococcus aureus* ATCC 29213 is presented in FIG. 3B. As it is observed, the microbial cells grow on plate after overnight incubation when the concentration of particles is equal to or less than 8 μg/mL. However, at 16 μg/mL, only a small number of cells have been able to grow and form colonies. At 32 μg/mL, 100% of bacteria were killed (no colony observed on the plate).

The antimicrobial surface exemplified by the agarose gel is an appropriate model system for an ideal antimicrobial surface, because the bulk portion of the gel is water and doesn't contribute to the potential shielding of the antimicrobial particles from contacting the bacterial cells. Moreover, the hydration layer on the surface facilitates the movements of bacteria thereby implying a larger zone of inhibition. Based on this reasoning we speculate that semisolid media such as agarose gel need less concentration of antimicrobial particles to inhibit bacterial growth in comparison to solid and hard surfaces such as implants where higher concentration of antimicrobial particles is needed to achieve the same bacterial growth inhibition and reliable antimicrobial activity. In the following we estimate the surface coverage for this ideal case.

Consider the agar dilution antimicrobial test corresponding to FIG. 3 where antimicrobial particles with an average size of 0.25 μm have been added to agarose gel with a concentration of 32 μg/mL. Assuming average particle radius of 0.25 μm and density of 7 $g/cm^3$. 32 μg/mL corresponds to a surface density of the particle of $2.27 \times 10^4$ particles/$cm^2$. This particle surface density is equivalent to the surface coverage of 0.45%. As it was mentioned above, this level of particle density may be an underestimation and higher amounts may be needed to ensure a good antimicrobial surface.

We also employed the method of Example 3B and measured the antimicrobial activity of $Ag_2O$ and $AgCl$ particles that had been obtained through high energy ball milling for 90 min.

The antimicrobial activity of the silver oxide particles was similar to the antimicrobial activity of nanostructured $AgNbO_3$ particles. However, the silver release from these particles through corrosion is at least 20 times higher, making them less suitable for inclusion in bone cement on the grounds of long-term potential cytotoxicity due to silver release to the surrounding tissues. In addition, the long-term antimicrobial activity of the cement incorporating $Ag_2O$ particles cannot be ensured as the particles at the interface are expected to eventually dissolve.

We speculated that $AgCl$ particles, having very low solubility and thereby releasing small levels of silver ions may be a candidate for inclusion in bone cements. However, it showed no noticeable antimicrobial activity against *Staphylococcus aureus* ATCC 29213 at the highest concentration of 32 μg/mL of the Agar dilution method according to the method of Example 3B.

The two observations above (meaning the case of $Ag_2O$ and $AgCl$ particles) highlights the selection criteria for the antimicrobial particle to be used in bone cement application.

We also verified that nanostructured $AgNbO_3$ particles are relatively safe for mammalian cells. In this respect, the effect of $AgNbO_3$ nanostructured aggregates on human cell line THP-1 was studied and it was observed that incubating these cells in a media containing up to 60 μg/mL of the nanostructured particles did not result in cytotoxicity or cell death. Also, no structural or morphological changes were observed upon exposure of cells such as MRC-5 (originated from human fibroblast) and Hep-2 (human epidermoid carcinoma) cell line to antimicrobial particles at concentration below 60 μg/mL.

After establishing the suitability of nanostructured $AgNbO_3$ particles for bone cement application we proceeded to prepare antimicrobial bone cement according to the approaches of the current invention and subjected it to various characterization tests.

We prepared bone cement with different w/w concentrations of nanostructured antimicrobial $AgNbO_3$ (20%, 10%, 5%, 2.5%, 1.2%) according to the method of Example 4. We noticed the following remarkable observations: 1) During the wetting stage, just after mixing the dry and liquid components, the nanostructured particles rapidly dispersed throughout the mixture giving rise to a characteristically dark color even for the case of 1.2% $AgNbO_3$. This observation is a likely indication that some spontaneous homogenizing mechanism that results in relatively homogeneous distribution of antimicrobial particles in the hardened cement; thus, adjustments in the established compositions of the dry and liquid components may not be required. 2) Some $AgNbO_3$ particles would come off the disc with 20% particle content when it was placed in water and vortexed. This indicates that unless the formulation of the starting ingredients is modified, incorporating excessive amounts of $AgNbO_3$ particles is associated with the risk of releasing some particles as wear debris. This may trigger a host cell response around the implants. Thus, the amount of $AgNbO_3$ particles mixed with pre-polymerized polymethyl methacrylate particles should be kept below 20%. In another embodiment the amount of $AgNbO_3$ particles mixed with pre-polymerized polymethyl methacrylate particles is kept below 10% w/w. In more preferred embodiment, the amount of $AgNbO_3$ particles mixed with pre-polymerized polymethyl methacrylate particles is kept below 4% w/w.

In order to evaluate the microstructure of hardened cements in terms of nanostructured $AgNbO_3$ particle distribution, we analyzed a PMMA sample having w/w $AgNbO_3$ concentration of 4% prepared according to method 4 using scanning electron microscopy according to the method of Example 5. Prior to performing microscopy, the axial region of the disk was subjected to polishing: It was manually and sequentially wet polished with silicon carbide papers of grid number 320, 400, 600, 800, followed by diamond suspension (Leco Corp) of 3 then 1 μm, and finally colloidal silica OP-U suspension (Struers). Then the polished region of the disk was coated with carbon to enable electron conductivity, a prerequisite of scanning electron microscopy. EDS mode of scanning electron microscopy was used to produce an elemental distribution map of the sample surface according to example 5.

Figure 4:
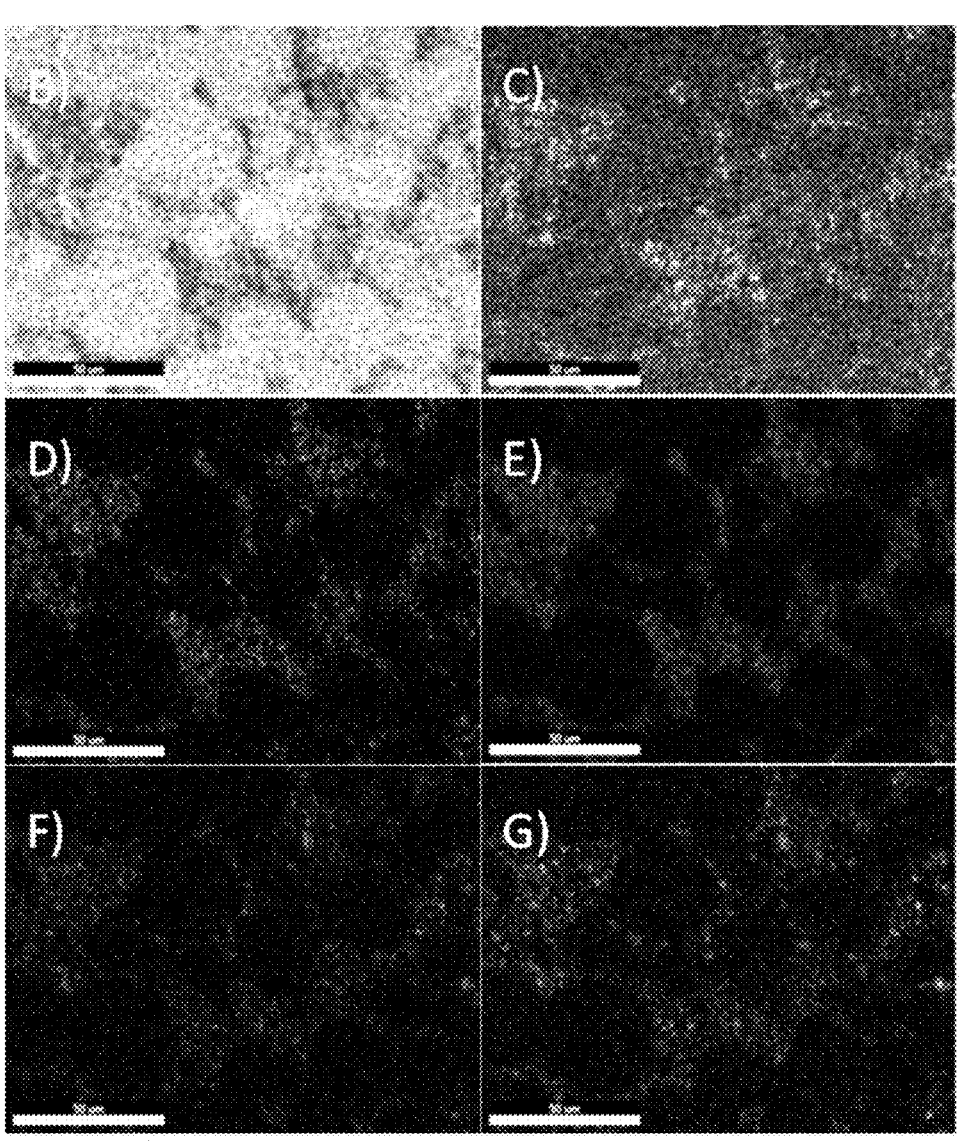
FIG. 4 presents the elemental map of PMMA disk with 4 w/w % NS_$AgNbO_3$: Picture B, C, D, E, F, and G show Carbon, Oxygen, Barium, Sulfate, Silver, and Niobium distribution respectively. Scale bar representing 50 μm.

A typical elemental distribution map is presented in FIG. 4. The areas rich in C likely indicate the PMMA particles from the dry component. Ag and Nb, representing $AgNbO_3$ particles, are mainly located between PMMA particles arranged in visibly uniform distribution without clumping. We repeated elemental analysis on multiple points throughout the disc surface and observed no significant inhomogeneity. This confirms that some mechanism helps with homogenizing nanostructured $AgNbO_3$ particles during wetting and hardening stages of the bone cement. Therefore, the risk of a part in the cement bone interface not receiving a sufficient number of antimicrobial particles is low.

In order to evaluate the silver release rate from antimicrobial discs, we prepared antimicrobial discs containing 4% w/w of $AgNbO_3$ particles according to the method of Example 4 and measured their silver release rate according to the method of Example 6. The results, which are presented in FIG. 5, showed that discs didn't release significant silver ions in deionized water. The concentration of released silver ions after 6 days in water was 0.24 ppm. The concentration of silver ions in water after 11 days increases very slightly (up to 0.25 ppm), indicating that the silver release from the $AgNbO_3$ loaded cement is not linear with time.

The antimicrobial activity of the cement with 1.2% w/w of $AgNbO_3$ particles was tested against Gram-positive *Staphylococcus aureus* ATCC 29213 and Gram-negative *Pseudomonas aeruginosa* ATCC 27853 according to the method of Example 7. While the bacterial cells spotted on the control disk (containing 0% of nanostructured $AgNbO_3$) had survived, the disc containing nanostructured $AgNbO_3$ had killed all bacterial cells. Accordingly, The experiment was repeated using a disc which had been stored in water for 55 days. It was found that the disc had retained its antimicrobial activity.

The biocompatibility of the antimicrobial discs was assessed in terms of cytotoxicity level and mechanical properties with respect to pure cement.

Figure 6:
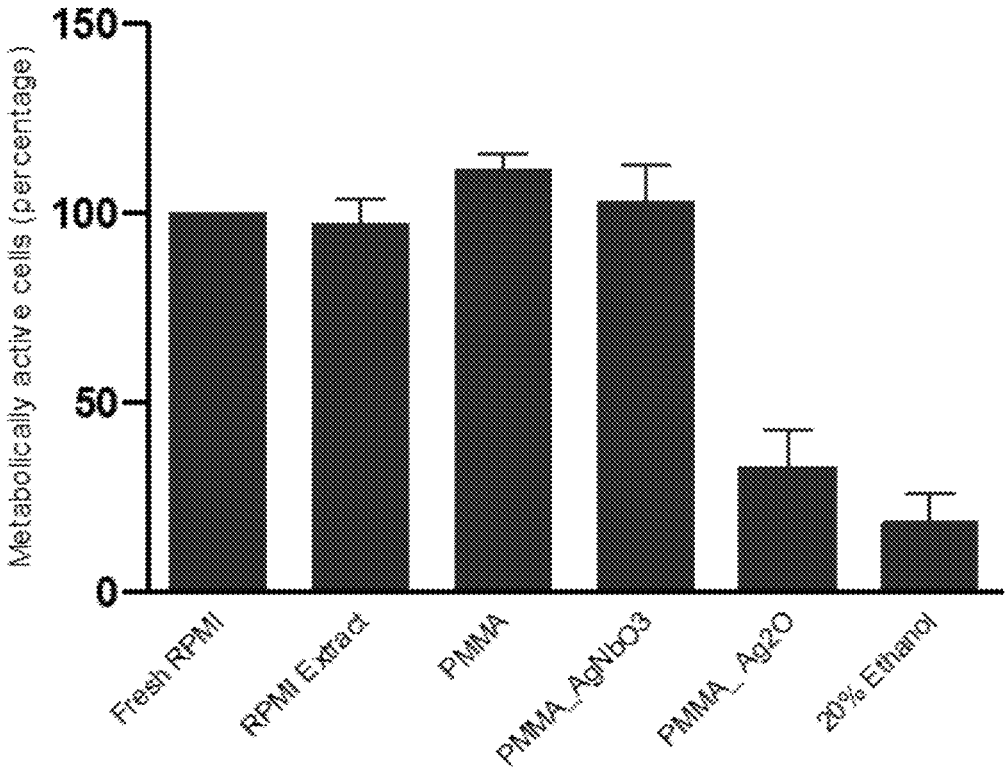
FIG. 6 Presents the cytotoxicity test results on extracts of the PMM_$AgNbO_3$, PMM_$Ag_2O$ and controls. PMM_$AgNbO_3$ and PMM_$Ag_2O$, respectively stand for bone cements loaded with 2% w/w of nanostructured antimicrobial perovskite ($AgNbO_3$) particles and of 2% w/w of $Ag_2O$ nanostructured particles. Extracts of PMMA disc and RPMI were used as control negatives. The graph shows the percentage of metabolically active macrophages after 24 h contact with the different sample extracts compared to control negative. Results are mean±SD from a minimum of three independent biological replicates.

The cytotoxicity test was performed according to the method of Example 8 for 2% w/w antimicrobial cement and pure PMMA. The result is presented in FIG. 6. The result indicates the antimicrobial cement incorporated with nanostructured $AgNbO_3$ particles, in contrast to the cement incorporated with $Ag_2O$ particles, was non-toxic against Macrophages.

The mechanical property tests were performed according to the methods of Examples 9, 10 and 11. The results are presented in FIGS. 7, 8, and 9. Based on these results, 4% w/w antimicrobial cement differs from pure PMMA to some extent. Thus, increasing the w/w ratio above 4% may require additional regulatory hurdles. However, this is not considered a hard limitation.

In one embodiment, w/w ratio is selected to be in the range of 1% to 10%. In another embodiment, w/w ratio is selected to be in the range of 2% to 8%. Still, in another embodiment w/w is selected to be in the range of 1.5% to 4%.

The methods described above may be employed for preparing antimicrobial polymer-based solids other than bone cement. In this case the preferred route for preparation would be to use two-component reagent concept: 1) Dry component having polymer beads and, optionally, other reagents such as polymerization initiator, and 2) Liquid component having monomer of the target polymer, and optionally other reagents such as stabilizers. The antimicrobial nanostructured particles are mixed with the dry component. The polymer-based solid is prepared by mixing the two components under appropriate conditions to allow the polymerization process proceeds. The antimicrobial nanostructured particles will disperse in the mixture before solidification. The amount of the added antimicrobial nanostructured particles relative to the weight of the dry component or the weight of the solid is determined by the desired antimicrobial activity level and the tolerable safety requirements.

EXAMPLES

The following examples are presented to enable those skilled in the art to understand and to practice embodiments of the present disclosure. They should not be considered as a limitation on the scope of the disclosure, but merely as being illustrative and representative thereof.

Example 1A: The Synthesis of $AgNbO_3$ Aggregates Employing Sol-Gel Method

A mixture of 0.01 mol, 4.47 g of Niobium ammonium oxalate ($C_4H_4NNbO_9 \cdot xH_2O$, Sigma-Aldrich Corp), 0.01 mol, 1.69 g silver nitrate ($AgNO_3$, Fisher Scientific International, Inc) and 8.40 g Citrate acid ($C_6H_8O_7$, Fisher Scientific International, Inc) were dissolved in 30 mL Hydrogen peroxide ($H_2O_2$, Fisher Scientific International, Inc). After adding 2 mL Nitric acid ($HNO_3$, Anachemia Canada, Inc), the mixture was kept at 65° C. for 1 h to decompose oxalate within niobium ammonium oxalate. Then, the pH value of the solution was adjusted to about 6.5 by dropping Ammonia ($NH_3$, VWR International, LLC) to obtain a yellowish solution. The precursor solution turned into a resin-like gel with a high viscosity by heating at 120° C. for several hours. The gel was treated at 300° C. for 2 h to burn out unnecessary organics, and then calcined at 550° C. for 2 h. The examination by XRD confirmed the formation of perovskite crystalline structure.

Example 1B. The Synthesis of $AgNbO_3$ Aggregates Employing Ceramic Method Followed by Mechanical Treatment The antimicrobial particles used in the current invention have a formula of $AgNbO_3$ and is synthesized by employing the solid-state method (also known as ceramic method). In the ceramic method, the perovskite oxide is synthesized from metal-oxide precursors by high-temperature heat treatment. The raw materials $Ag_2O$ (Sigma-Aldrich Corp) and $Nb_2O_5$ (Inframat® Advanced Materials LLC), with the weight ratio of 1 gram to 1.147 gram respectively (for each gram of $Ag_2O$, 1.147 gram of $Nb_2O_5$ powders), are mixed in a hardened steel crucible with high energy ball milling for 10 minutes. The mixture is transferred to a ceramic crucible and placed in an oven where it is gradually heated at a rate of 5° C./min until the formation temperature, 1000° C., is reached. The mixture is kept at this temperature for about 4 hours and gradually cooled down at a rate of 10° C./min to room temperature. The powder was subjected to high energy ball milling. The milling process was carried out using the 8000D Mixer/Mill® (SPEX SamplePrep, LLC) in which 7 g of material was agitated at 1060 cycles per minute for durations of up to 90 minutes. The apparatus system also contains a supporting crucible and typically three milling balls. The crucible chosen was the 8001 hardened steel vial set, which contains a vial size of 2¼ inch. Dia.×3 inch, the vial body and cap liner. Two ½ inch, and one ¼ inch. steel balls were used for grinding. The powder was subjected to a low energy attrition mill. In this step, approximately 40 g of powder from the previous step (agglomerates) was added to a crucible containing hundreds of steel beads of 4.5 mm in diameter, which were made to rotate at 90 rpm by Szegvari Attritor System Type E Model 01-STD (Union Process, Inc.). To this, 10 mL of water (or alcohols such as ethanol) was added and the attrition process was performed for a selected time duration. At the end of the operation the beads are rinsed with deionized water and the residue thus obtained was dried inside an oven with a temperature of 150° C. overnight.

Example 2A: Measuring Particle Size Distribution of Nanostructured Aggregates The size and morphology of nanostructured aggregates was studied with Dynamic Light Scattering (DLS) as described below. A 0.01 mg/mL suspension of $AgNbO_3$ particles in distilled water was subject to 10-minute ultrasound (Fisher Scientific FS530H), followed by 1-minute vortex (VWR Analog vortex mixer) for homogenous particle distribution. A 40 µL aliquot of the sample was added to the DLS sample holder (ZEN0040 disposable microcuvette) and the 3 replicates per sample were performed by Malvern ZEN1600 DLS analyzer, with the following parameters: Nanoparticle refractive index of 1.96, Temperature of 25° C., and Equilibrium for 2 minutes.

Example 2B: Measuring Specific Surface Area of Nanostructured Aggregates

The specific area of nanostructured aggregates was measured with a TriStar II 3020 (Micromeritics Instruments Corp) instrument as the following: 250 mg of nanoparticles was degassed at 300° C. for an overnight time period. Then, the input parameters on the software were selected as:
1. Surface area and pore size powder for analysis condition
2. Adsorptive gas: Nitrogen at 77.35 K
3. The measurement was reported for N2 gas. The instrument's software TriStar II 3020 Version 3.02 performed statistical analysis and reported specific surface area in m2/g units.

Example 2C: Measuring Silver Ion Release Rate

The test was performed by pouring the particles in 1 L of deionized water in a glass beaker. First, two 10 mL replicate samples were taken from the beaker and were marked as blank. Next, 500 mg of particles was added to the beaker. The beaker was then sealed with parafilm and aluminum paper cover to prevent evaporation or effects of light. At time points (2, 7, 14, 21, 28, 35) days, two 10 mL replicate samples were taken from the beaker and 20 mL of deionized water was added to the beaker to compensate for the removed volume. The collected samples were analyzed for silver ion concentration by Avio 200 ICP-OES (PerkinElmer). Prior to testing, each of the samples were dosed with 1 mL of 5% nitric acid solution to help wash silver particles from sample tube walls. The obtained values of the ICP measurement were based on a calibration curve drawn using $AgNO_3$ with $Ag^+$ equivalent of 1-100 ppm and set to record the emission line for $Ag^+$, at 328 nm. Each sample measurement was performed in three replicates and averaged.

Example 3A: Measuring Antimicrobial Activity by Broth Microdilution Method

The broth microdilution antimicrobial susceptibility test (AST) involves growing bacterial cells inside a series of wells on a microwell plate containing growth media. Each well was supplied with different concentrations of the antimicrobial agent, differing by a factor of two from one well to the next. Known number of bacterial cells in the range of $10^5$ CFU (CFU=colony forming unit, meaning a cell that is viable and can divide) was dispensed into each well. After overnight incubation, the wells were inspected for signs of growth by visual inspection or turbidimetry. Thus, the minimum concentration required to inhibit growth was determined and reported as minimum inhibitory concentration (MIC) value.

Example 3B: Measuring Antimicrobial Activity by Agar Dilution Method

In order to measure the MIC values by Agar dilution method, agarose petri dishes with different concentrations of antimicrobial agents, differing by a factor of 2, were prepared as follows. In another tube an antimicrobial solution (suspension in the case of nanoparticles) with a concentration of 20 times the target concentration was prepared in water. The agarose gel was autoclaved and allowed to cool down in a water bath having a temperature of 50° C. 1 mL of the particle suspension was mixed with 19 mL of the gel, poured into a petri dish and allowed to solidify. Then, following the CLSI guidelines, a suspension of target microbial cells was streaked on each petri dish and incubated overnight. The petri dishes were inspected and the antimicrobial concentration at which colony growth was inhibited was reported as the MIC value.

Example 4: Preparing Antimicrobial Bone Cement Disk

This example aims at providing a method for preparing antimicrobial bone cement discs, which are used for evaluating the antimicrobial activity of the bone cement. For the control cement disk, cement powder (Surgical simplex P radiopaque powder, Stryker) was mixed with a liquid monomer (Simplex P liquid, Stryker) at 10 g and 5 mL, respectively. This was cast in a silicone mold with an inner diameter of 12 mm and depth of 3 mm. After solidification, the disc was pushed out of the mold and used in experiments. The approximate weight of each disc was 300 mg.

For the cement disk loaded with $AgNbO_3$, 10 g cement powder was mixed with different amounts of $AgNbO_3$ to obtain the desired W/W ratio. Then 5 ml of liquid monomer was added to the mixture and mixed quickly until a homogenous paste was formed which was immediately cast in a silicone mold with an inner diameter of 12 mm and depth of 3 mm. After solidification, the disc was pushed out of the mold and used in subsequent experiments The approximate weight of each disc was 300 mg.

Example 5. Electron Microscopic Evaluation of Antimicrobial Discs

Scanning electron microscopy (SEM) images of the polished disk surfaces were obtained using a Tescan Vega 3.

Secondary electron (SE) imaging mode was used to acquire a topographic view of the disk surface. Backscatter electron (BSE) imaging mode was used to differentiate the atoms present on the surface of the sample based on their atomic number. The imaging was performed over a potential of 10 kV and magnification levels of 50×, 150×, 500×, 1500×, 5000×. It is hard to differentiate Ba and Sa from Ag and Nb in BSE images, all these atoms appear as white speckles. To effectively differentiate them from one another and to detect the spread of $AgNbO_3$ over the surface of the disks, EDS was performed with an EDAX Element EDS Detector. For all of the tests, an X-ray energy detection range of 0-7 eV, a resolution of 128.8 eV and magnification of anywhere between 150× to 15000× and a beam intensity between 10 and 15 was selected. The composition of selected elements, including Ag, Nb S, Ba, C, and O, were reported for each disk.

Example 6: Measuring Silver Release Rate from the Antimicrobial Bone Cement Disk This example aims at quantifying the silver release rate from the antimicrobial bone cement disk, which was prepared following the method of example 4. The disc was placed in 10 mL deionized water in a falcon tube. At the end of the desired period, the disc was removed from the tube and the water was analyzed using an atomic emission spectrometer (Agilent MP-AES model 4200).

Example 7: Measuring the Antimicrobial Activity of Cement Discs

This example aims at measuring the antimicrobial activity of cement discs, which was prepared following the method of example 4. The cement disc was sterilized by soaking it in 70% isopropanol for one minute, washed in sterile water and allowed to air dry. A few colonies form a fresh overnight culture of test bacterium was used to make a 0.5 McFarland cell suspension in saline, which was then diluted 1/100 in TSB liquid culture medium. The disc was put on a sterile surface and its axial surface was loaded with 50 microliter of bacterial cell suspension (this is roughly around 80000 bacterial cells) and was allowed to air dry. The disk was then dropped in a tubes of 5 mL TSB and incubated at 35° C., with 5% $CO_2$ for 18-24 h post-incubation. The tube was checked visually for signs of growth (turbidity) or lack of growth (clear medium). In addition to the visual inspection, 50 μL from the tube was sub-cultured onto a blood agar plate, which was then incubated at 37° C., with 5% $CO_2$ for 18-24 h. Post-incubation, the plate was checked visually for bacterial growth represented by colonies on the surface of the blood agar plate.

Example 8: Measuring Cytotoxicity of Cement Discs

The Indirect Cytotoxicity Assay was performed according to standard method ISO 10993 of medical devices to evaluate the biocompatibility of test samples after indirect contact. Extracts of discs were used in the cytotoxicity test. These extracts are prepared after incubation of test discs for 72 h at 37° C. in Roswell Park Memorial Institute culture media (RPMI-1640) supplemented with 10% FBS, 2 mM glutamine, 100 IU/ml Penicillin and 100 mg/ml Streptomycin. The Cytotoxicity of these extracts was assessed against THP1 macrophages. Briefly, THP-1 cells were cultured in RPMI-1640 medium and differentiated by incubation for two days in medium containing 20 ng/ml Phorbol-12-Myristate-13-Acetate (PMA) before being incubated with the extracts. After incubation for 24 h at 37° C. with 5% $CO_2$, Resazurin was added, and the absorbance was read simultaneously at 570 and 600 nm to monitor viability of the cells. The results are presented as a percentage of the viability of the cells. The results were standardized based on the absorbance of fresh RPMI-1640 as 100%.

Example 9: Compressive Test

Compressive tests were performed following the ASTM D695 norm, standard test method for compressive properties of rigid plastics. The test specimens for compressive strength measurements were in the form of a right cylinder with a length of 25.42 mm and diameter of 12.00 mm. Given the fact that PMMA is an isotropic material, five specimens of each sample were tested. Specimen conditioning and test conditions were conducted following standard laboratory atmosphere as defined by ASTM D618. The specimen was placed between the surfaces of the compression tool of a SATEC T20000 universal testing machine, taking care to align the centerline of the of the specimen's long axis with the centerline of the compression tool plunger and to ensure the ends of the specimen are parallel with the surface of the compression tool. The speed control of the compression tool was then set to 1.00 mm/min and the complete load-deformation curve of the test specimens were recorded.

Compressive strain values were obtained by dividing the corresponding deformation value by the length of the test specimen along its longitudinal axis and expressed as percentage. Compressive stress values were obtained by dividing the corresponding load by the area of the cross section of the specimen and expressed as a force per unit area. Using the set of compressive stress and strain values, stress-strain diagrams were generated and presented in FIG. 2. Using this data, four key values were noted. The first among which was compressive yield strength, defined as the stress value corresponding to the first point on the stress-strain diagram at which an increase in strain occurs without an increase in stress. The strain value during the compressive yield strength was also noted. Next was the compressive strength, defined as the maximum nominal compressive stress carried by a test specimen during a compression test. The corresponding strain value was noted. These four key values were averaged for each of the sample formulations.

Example 10: Measuring the Fatigue of Cement Discs

Fatigue tests on solidified bone cement were performed under tension-tension mode using an Acumen 3 (MTS) machine. For each sample composition, six multipurpose test specimens were prepared with dimensions and shape conforming to the norm ISO 527 type 1B. The dumb-bell shaped specimens were 150 and 60 mm in length for overall and narrow sided portion respectively, 20.0 and 10.0 mm in width at ends and narrow portion respectively, and a thickness of 4.0 mm. The quality of the fatigue test results is dependent on minimizing the variation of specimen thickness to within a tolerance of 0.2 mm, which was done by compression molding the sample during preparation. Briefly, an aluminum 6064 based mold was sprayed with TraSys® 420 mold release agent, and heated to 100° C. for 5 minutes to evaporate the residuals. Next, the raw ingredients of the PMMA mixtures were mixed and poured onto the mold. Whilst in viscous state, a non-stick Teflon sheet and a steel plate were placed over the mold, and the entire assembly compressed using a model C laboratory press (Carver, inc) at a clamping force of 4800 lb, corresponding to a pressure of 10 MPa. This pressure was maintained to within 10% until the PMMA solidified, in accordance with ISO 293. For fatigue tests, one specimen at a time was placed between clamps distanced 50 mm from one another. The test was performed at room temperature under cyclic load at a frequency of 5 Hz, to avoid adiabatic heating of the PMMA sample. The R-ratio was fixed at 0.3, with strain amplitudes ranging between 0.1575 to 0.63. Using the instrument's software win7, the raw data for force and deformation of the specimen was recorded at a sampling rate of 200 points per sinusoidal cycle, further data treatments were performed using a custom written Python code.

Example 11: Measuring Hardness of Bone Cement Samples

Hardness tests on PMMA, PMMA loaded with 2% NS_AgNbO3, and PMMA loaded with 4% NS_AgNbO3 were performed following the ISO 2039-2 norm, which is a method for determining the indentation hardness of plastics by means of the Rockwell hardness tester. In this case, the Rockwell L hardness scale was tested. Briefly, a RT-120 (LECO corp) hardness tester was mounted on a level, rigid base free from vibration. The specimens consisted of two 4 mm flat sheets stacked one on top of the other, for a total of 8 mm in thickness, with minimal variation in thickness. This was achieved by compression molding, a procedure previously described in the fatigue testing methodology. Additionally, the specimens were large enough that 5 indentations could be made, each 10 mm apart from one another, Although ISO 2039-2 considers one test specimen to be sufficient for determination of Rockwell hardness, in this study three separate specimens were tested for each composition, with 5 measurements made on each specimen. The conditioning of the test specimens was performed according to what is specified in ISO 291, and the hardness testing was performed in the same standard atmosphere as used for conditioning the test specimen. The test specimens were placed on the platform, normal to the direction of the applied load. A constant minor load of 98.07 N was applied to a 6.35 mm steel ball resting on the specimen. Within 10 s of applying the minor load, the major load of 588.4 N was applied. The major load was removed 15 s after the start of applying the major load. The major load was then released to return back to the minor load, and within 15 s after the start of removing the major load, the Rockwell L value was read. The Rockwell measurement is based on the total depth of penetration, minus the elastic recovery after a fixed time following the removal of the major load, minus penetration resulting from the minor load.

The invention claimed is:
1. An antimicrobial bone cement, comprising:
a dry mixture including a dry component and nanostructured antimicrobial silver perovskite particles, wherein a weight of the nanostructured antimicrobial silver perovskite particles is in a range of 1% to 10% of a total weight of the antimicrobial bone cement; and
the nanostructured antimicrobial silver perovskite particles having a specific surface area of at least 1 m$^2$/g and a silver release rate of less than 0.1% of the total weight over 24 hours into deionized water at room temperature.

2. The antimicrobial bone cement of claim 1, wherein the nanostructured antimicrobial silver perovskite particles is AgNbO$_3$.
3. The antimicrobial bone cement of claim 1, wherein the nanostructured antimicrobial silver perovskite particles is AgTaO$_3$.
4. The antimicrobial bone cement of claim 1, wherein the specific surface area of the nanostructured antimicrobial silver perovskite particles is 1 m$^2$/g to 40 m$^2$/g.
5. The antimicrobial bone cement of claim 1, wherein the specific surface area of the nanostructured antimicrobial silver perovskite particles is 2 m$^2$/g to 20 m$^2$/g.
6. The antimicrobial bone cement of claim 1, wherein the specific surface area of the nanostructured antimicrobial silver perovskite particles is 4 m$^2$/g to 10 m$^2$/g.
7. The antimicrobial bone cement of claim 1, wherein the weight of the nanostructured antimicrobial silver perovskite particles is 1% to 8% of the total weight of the antimicrobial bone cement.
8. The antimicrobial bone cement of claim 1, wherein the weight of the nanostructured antimicrobial silver perovskite particles is 1% to 4% of the total weight of the antimicrobial bone cement.
9. The antimicrobial bone cement of claim 1, wherein the antimicrobial bone cement is polymethyl methacrylate (PMMA).
10. The antimicrobial bone cement of claim 1, wherein the dry component consists of an acrylic polymer and a polymerization initiator.
11. The antimicrobial bone cement of claim 1, further comprising a liquid component which is added to the mixture of the dry component and the nanostructured antimicrobial silver perovskite particles to form the antimicrobial bone cement.
12. The antimicrobial bone cement of claim 11, wherein the liquid component consists of an acrylic monomer and a polymerization inhibitor.
13. The antimicrobial bone cement of claim 1, wherein the nanostructured antimicrobial silver perovskite particles exhibit long-lasting, broad-spectrum antimicrobial activity.
14. The antimicrobial bone cement of claim 13, wherein the nanostructured antimicrobial silver perovskite particles maintain their antimicrobial activity after long-term exposure to an external environment.
15. The antimicrobial bone cement of claim 1, wherein the nanostructured antimicrobial silver perovskite particles have a relative silver release rate (RSRR) of less than 20%.
16. The antimicrobial bone cement of claim 1, wherein the nanostructured antimicrobial silver perovskite particles have a relative silver release rate (RSRR) of 1% to 15%.
17. The antimicrobial bone cement of claim 1, wherein antimicrobial activity of the nanostructured antimicrobial silver perovskite particles is mediated by continuous change in silver oxidation valence in proximity to microorganisms.
18. A method for preparing the antimicrobial bone cement of claim 1, comprising:
adding a liquid component to the dry mixture of the dry component and the nanostructured antimicrobial silver perovskite particles.
19. The method of claim 18, wherein the dry component and the nanostructured antimicrobial silver perovskite particles are pre-packaged together.
20. A method for preparing the antimicrobial bone cement of claim 1 for application, the method comprising:
providing the dry component comprising polymethyl methacrylate particles and a polymerization initiator;

providing a liquid component comprising a liquid monomer of methyl methacrylate, an accelerator, and a stabilizer;

providing the nanostructured antimicrobial silver perovskite particles having the specific surface area of at least 1 m$^2$/g and the silver release rate of less than 0.1% of their total weight over 24 hours into the deionized water at room temperature; and premixing the nanostructured antimicrobial silver perovskite particles with the dry component to form the dry mixture, wherein the dry mixture and the liquid component are configured to be mixed in an operation room immediately before application of the antimicrobial bone cement.

*     *     *     *     *